United States Patent [19]

Faulds et al.

[11] Patent Number: 4,985,243
[45] Date of Patent: Jan. 15, 1991

[54] COMPOSITION AND METHOD FOR PROTECTING AGAINST DISEASES CAUSED BY MICROORGANISMS

[75] Inventors: Daryl H. Faulds; Mimi Vishoot, both of Millbrae, Calif.

[73] Assignee: ML Technology Ventures, L.P., New York, N.Y.

[21] Appl. No.: 146,256

[22] Filed: Jan. 20, 1988

[51] Int. Cl.$^5$ .................. A61K 39/305; A61K 39/00; A61K 37/54; C12N 9/22
[52] U.S. Cl. ...................... 424/85.8; 424/88; 424/94.6; 435/199; 435/870
[58] Field of Search ............ 424/92, 94.6, 85.8, 424/88; 435/870, 199

[56] References Cited

U.S. PATENT DOCUMENTS 3,485,721  12/1969  Woodhour et al. ............ 435/870
4,123,427  10/1978  Daniel ........................ 424/92
4,666,851   5/1987  Lee .......................... 435/870

OTHER PUBLICATIONS

Nicolet et al., Res. Vet. Sci., 1980, 29, 305–309.
Minion et al., Chem. Abstracts, vol. 104:48450q (1986).

Primary Examiner—Jacqueline Stone
Attorney, Agent, or Firm—Elliot M. Olstein; Raymond J. Lillie

[57] ABSTRACT

A vaccine for protecting against a disease caused by a microorganism which does not synthesize nucleic acid precursors such as a Micoplasma organism, which contains nuclease and/or a nuclease fragment or derivative which produces antibodies which recognize nuclease secreted or available on the surface of the microorganism against which protection is to be afforded. A vaccine may also be prepared from an antibody or fragment or derivative thereof which recognizes such nuclease of such microorganism.

14 Claims, No Drawings

COMPOSITION AND METHOD FOR PROTECTING AGAINST DISEASES CAUSED BY MICROORGANISMS

This invention relates to a composition and method for protecting against diseases caused by microorganisms. Still more particularly, the invention is directed to a composition and method for protecting against diseases caused by microorganisms which lack biosynthetic pathways for nucleic acid precursors in particular mycoplasma organisms and most particularly mycoplasmal pneumonia of swine caused by *M. hyopneumoniae*.

There are diseases which are caused by various microorganisms; for example mycoplasma organisms. The disease caused by *Mycoplasma hyopneumoniae* (in particular in swine), occurs throughout the world and is a disease associated with the loss of swine. The disease generally results in inefficient, stunted and sickly animals, and effected swine are often prone to secondary infection by opportunistic microorganisms.

There have been numerous attempts to provide a vaccine for protecting swine against mycoplasmal pneumonia; however, such vaccines have not been successful.

Kristensen et al. in *Am. J. Vet. Res.* 42 (1981) page 784, found no protection of swine against mycoplasmal pneumonia after injection with heat inactivated cells of *Mycoplasma hyopneumoniae*.

Etheride, et al *Res. Vet. Sci.* 33 (1982) page 188 found incomplete protection against lung colonization by Mycoplasma when a live vaccine was given intravenously, subtutaneously or intraperitoneally.

Ross et al. *Am. J. Vet. Res.* 45 (1984) page 1899 disclosed that the use of *Mycoplasma hyopneumoniae* extracts prepared by a freeze thaw procedure provided only variable protection and, in some instances, enhanced lesion development. Ross et al. also claimed that injection of such agent into swine gave some level of protection against an intratrachael challenge exposure consisting of 4 ml of supernate from a 10% suspension of pneumonic lung containing strain VPP-11 combined with 1 ml of a 24 hour culture of 15 to 20 passage of the same strain.

As a result, to date, an effective vaccine for protecting swine against mycoplasmal pneumonia has not been developed.

In accordance with one aspect of the present invention, there is provided a composition and a method for protection against diseases caused by microorganisms.

In accordance with one aspect of the present invention, there is provided a composition and method for protecting against diseases caused by microorganisms which lack biosynthetic pathways for nucleic acid precursors (purines and/or pyrimidines) by use of a nuclease (nucleic acid degrading enzyme) and/or fragment and/or derivative thereof which produces antibodies having paratopes which recognize nuclease which is secreted by and/or exposed on an external surface of the microorganism against which protection is to be afforded (such secreted nucleases and/or nucleases exposed on the external surface of the cell are referred to herein as "extrinsic nuclease(s)").

The nuclease may be a deoxyribonuclease (DNA degrading enzyme or DNase) and/or a ribonuclease (RNA degrading enzyme or RNase) and/or fragment and/or derivative thereof which produces antibodies which recognize, in the case where an RNase or fragment thereof is used, RNase secreted by and/or exposed on the surface of the microorganism against which protection is to be afforded (extrinsic RNase), or which produce antibodies which recognize, in the case where a DNase and/or DNase fragment and/or derivative is administered, DNase secreted by and/or exposed on the surface of the microorganisms against which protection is to be afforded (extrinsic DNase).

The fragment and/or derivative of RNase or DNase which is employed may or may not have enzymatic activity as long as such fragment and/or derivative is capable of producing antibodies of the type hereinabove described.

Although the present invention is not to be limited by any explanation, it is believed that certain organisms which are not capable of synthesizing nucleic acid precursors require the presence of nuclease to obtain purines and pyrimidines required for growth and infection; that nuclease secreted by and/or exposed on the surface of the cell functions to produce purines and pyrimidines from nucleic acids provided by the host cells. The administering of an appropriate nuclease(s) and/or fragment(s) and/or derivative which induce the production of antibodies having paratopes which recognize extrinsic nuclease specifically bind or remove the extrinsic nuclease thereby providing protection against growth of and infection by the microorganism. Thus, by inducing in the animal the production of antibodies which recognize extrinsic RNase and/or extrinsic DNase of the microorganism against which protection is to be afforded, growth of and infection by such microorganism may be eliminated or retarded.

In some cases protection may be afforded by use of either DNase or fragment and/or derivative thereof or RNase or fragment and/or derivative thereof. In other cases, protection may be afforded only by using RNase (or fragment and/or derivative thereof) or only by using DNase (or fragment and/or derivative thereof). In some cases, it may be necessary to administer both RNase and DNase (or appropriate fragments and/or derivative). As should be apparent, such use is dependent on whether or not the microorganism requires RNase, DNase or both to produce the purines and pyrimidines required for growth and infection. The preferred DNase or fragment and/or derivative thereof is a DNA endonuclease.

As representative examples of microorganisms against which protection is to be afforded in accordance with the present invention, there may be mentioned; mycopolasmas, acholeplasmas, ureaplasmas, spiroplasmas and aneroplasmas.

The nuclease used for providing protection may be obtained from the micoorganism against which protection is sought by recovering extrinsic nuclease from the organism. As a further alternative, a recombinant DNA molecule encoding for an amino acid sequence having one or more antigenic determinants (epitopes) of the extrinsic nuclease of the microorganism against which protection is sought may be employed for producing the nuclease or fragment and/or derivative thereof by genetic engineering techniques. Such nuclease or fragment and/or derivative thereof which is produced by genetic engineering techniques should produce antibodies which recognize extrinsic nuclease of the microorganism against which protection is sought; i.e., an immune response.

In accordance with a preferred embodiment, the present invention is directed to protecting against diseases caused by mycoplasma organisms. In accordance with a preferred embodiment such protection is afforded by the use of DNase or fragment and/or derivative thereof and preferably the DNase is a DNA endonuclease.

The present invention will be further described with respect to protecting against diseases caused by mycoplasma by the use of DNase or fragment or derivative thereof; however, such teachings are equally applicable to protecting against other microorganisms of the type hereinabove described and/or to the use of RNase.

The DNase used in the vaccine may be derived from the Mycoplasma organism; i.e., the DNase may be recovered from the membrane of the Mycoplasma organism by use of a mild detergent, such as a non-ionic detergent to solubilize the DNase.

The non-ionic detergent is employed in amounts which are sufficient to solubilize the DNase. In general, the weight ratio of non-ionic detergent to Mycoplasma organism portion which is subjected to treatment is from 0.05 to 1 to about 10.0 to 1, and preferably from about 0.5 to 1 to 5.0 to 1. The treatment is generally effected at a temperature which does not exceed 40° C. with the temperature most generally being in the order of from 1° C. to 37° C.

The treatment is for a time sufficient to effect solubilization of the DNase and in general, such time is in the order of from 0.5 to 18 hours; however, in some cases, longer or shorter times may be employed.

The solution employed to solubilize the DNase generally has an ionic strength of from 0.05 to 1.0M salt. A preferred solubilizing agent contains 0.2M sodium ion.

As hereinabove indicated, in general, the membrane of the Mycoplasma organism is subject to such treatment. Such membrane may be obtained by disrupting the organism by procedures generally known in the art, such as a freeze-thaw cycle; sonication; etc. Alternatively, the DNase may be derived from the whole organism. The selection of a suitable procedure is deemed to be within the scope of those skilled in the art from the teachings herein.

DNase may also be recovered from the supernatant of a mycoplasma cell culture; e.g., by precipitating DNase from the cell supernatant with ammonium sulphate.

As a further alternative, the DNase or fragment or derivative thereof may be obtained by genetic engineering techniques; for example by use of a recombinant DNA molecule which encodes for a nuclease or fragment or derivative thereof (in particular a DNase or fragment or derivative thereof) which produces antibodies having paratopes which recognize an extrinsic nuclease of the microorganism against which protection is sought.

The present invention provides a vaccine for protecting animals, in particular non-human animals against diseases caused by microorganisms of the type described; in particular mycoplasma organisms, by use of nuclease (or fragment or derivative thereof) which generates antibodies which recognize extrinsic nuclease found in the organism against which protection is sought. Thus, the nuclease (or fragment or derivative thereof) which is used to protect swine against mycoplasma organism would have one or more epitopes of the extrinsic DNase present in porcine mycoplasma.

The DNase may be derived directly from the organism, or may be produced by genetic engineering.

It is possible within the spirit and scope of the present invention to employ a fragment or derivative of nuclease in producing a vaccine of the present invention even though such fragment or derivative does not possess enzymatic activity. The term fragment or derivative of nuclease (RNase or DNase) as used herein is a fragment or derivative of nuclease (Rnase or DNase) which includes an epitope which will produce an antibody which recognizes the extrinsic nuclease (extrinsic RNase or DNase) of the organism against which the vaccine is to provide protection.

A vaccine for protection against diseases caused by organisms of the type hereinabove described, for example a Mycoplasma organism such as mycoplasmal pneumonia, and in particular for protecting swine against mycoplasmal pneumonia, is comprised of a nuclease, such as, DNase, and/or a fragment or derivative thereof, as hereinabove described, in combination with a suitable physiologically acceptable vehicle; e.g. a carrier and/or adjuvant. Such nuclease and/or fragment or derivative is employed in the vaccine in an amount effective to provide protection against a disease caused by the microorganisms, e.g. a Mycoplasma organism and in particular mycoplasmal pneumonia caused by *M. hyopneumoniae.*

In general, the vaccine contains at least 5 micrograms per dose and preferably at least 100 micrograms per dose of such nuclease, such as DNase and/or fragment or derivative. In most cases, the vaccine does not include the nuclease, and/or fragment or derivative in an amount greater than 20 milligrams.

If multiple doses are employed, in general, the vaccine would not be administered in an amount which exceeds 3 doses over 8 weeks.

The term "protection" or "protecting" when used with respect to the vaccine or methods described herein means that the vaccine prevents a disease caused by the organism, in particular mycoplasmal pneumonia caused by *M. hyopneumoniae* and/or reduces the severity of a disease caused by the organism, in particular mycoplasmal pneumonia caused by *M. hyopneumoniae.*

The vehicle which is employed in conjunction with the nuclease and/or fragment or derivative may be any one of a wide variety of vehicles. As representative examples of suitable vehicles, there may be mentioned: mineral oil, alum, synthetic polymers, etc. Vehicles for vaccines are well known in the art and the selection of a suitable vehicle is deemed to be within the scope of those skilled in the art from the teachings herein. The selection of a suitable vehicle is also dependent upon the manner in which the vaccine is to be administered. The vaccine may be in the form of an injectable dose and may be administered intramuscularly, intravenously intratracheally, intraperitoneally, intranasally, e.g. as an inhalent, or intraoccularly, or by sub-cutaneous administration. It is also possible to administer the vaccine orally by mixing the active components with feed or water; providing a tablet form, etc.

Other means for administering the vaccine should be apparent to those skilled in the art from the teachings herein; accordingly, the scope of the invention is not limited to a particular delivery form.

It is also to be understood that the vaccine may include active components or adjuvants in addition to the nuclease or fragments or derivatives hereinabove described.

It is also to be understood that the vaccine may include a combination of active components; e.g., a mixture of appropriate nuclease fragments or a mixture of nuclease and nuclease fragment, etc.

The vaccine is generally employed in non-human animals which are susceptible to diseases caused by Mycoplasma organisms, particularly mycoplasmal pneumonia caused by *M. hyopneumoniae*, and in particular in swine, and bovines.

In accordance with another aspect of the present invention, there is provided a composition and method for protecting animals against diseases caused by microoganisms of the type hereinabove described by use of an antibody or antibody fragment or derivative having paratopes which are recognized by extrinsic nuclease of the micoorganism against which protection is to be afforded.

The antibody may be produced from a nuclease (RNase or DNase) having the characteristics hereinabove described by procedures known in the art and such antibody may be either a monoclonal or polyclonal antibody. The antibody or appropriate fraction or derivative thereof may be employed for affording protection.

The antibody may be employed in a composition and administered as hereinabove described with reference to the use of a nuclease and/or nuclease fragment or derivative. In using an antibody or antibody fragment or derivative, the vaccine generally contains at least 5 micrograms per dose and preferably at least 50 micrograms per dose of such antibody or fragment or derivative. In most cases, the unit dosage dose does not exceed 20 milligrams.

Thus, in accordance with this aspect of the present invention, antibodies which recognize extrinsic nuclease of the microorganism against which the animal is to be protected are produced externally of the animal and such antibodies or fragments or derivative thereof, are administered to the animal to afford protection to the animal.

In accordance with a further aspect of the present invention, there is provided a DNase or fragment or derivative thereof in substantially pure form which produces antibodies which recognize extrinsic DNase of *M. hyopneumoniae*. Such DNase or DNase fragment includes one or more epitopes present in the extrinsic DNase of *M. hyopneumoniae*.

Such DNase may be recovered directly from the *M. hyopneumoniae* organism, as hereinabove described, and purified to obtain substantially pure DNase.

It is also possible within the spirit and scope of the present invention to produce such DNase by genetic engineering principles in which case the *M. hyopneumaniae* DNase or fragment or derivative thereof of the present invention could be produced in an organism other than *M. hyopneumoniae* e.g., by use of a recombinant DNA molecule encoding an amino acid sequence which produces antibodies which recognized extrinsic DNase of *M. hyopneumoniae*.

The extrinsic *M. hyopneumoniae* DNase is further characterized by:

A. Thermal lability. The cell surface DNase is inactivated by incubation at 56° C. for 10 minutes.
B. Trypsin sensitivity. The cell surface DNase activity is abolished by treatment of intact cells with trypsin.
C. Apparent molecular weight. When subjected to SDS polyacrylamide gel electrophoresis the enzyme runs as a doublet with an apparent molecular weight of 35 to 40 kDa.
D. Ion exchange characteristics. The DNase binds to DEAE-cellulose in 0.0175M NaCl and may be eluted with a NaCl gradient of 0.0175M to 0.5M. The DNase binds to phosphocellulose in 0.0175M NaCl and may be eluted with a NaCl gradient of 0.0175M to 1.0M.

The present invention will be further described with respect to the following examples; however, the scope of the invention is not to be limited thereby:

EXAMPLE 1

*Mycoplasma hyopneumoniae* strain VPP-11, strain J, or P-57223 is grown in 3.5 liters of Friis medium to a density of approximately $10^9$ to $10^{10}$ color changing units per ml. The cells are harvested by centrifugation, washed four times in phosphate buffered saline (PBS), and lysed in 10 mM Tris pH 8.0, 10 mM EDTA by repeated freeze-thaw cycles. Debris is removed by centrifugation at 12,000 g for 10 minutes. The membranes are harvested by centrifugation at 105,000 g for 45 minutes, washed once in PBS, and solubilized by 1.0% Triton X-100 in PBS for 18 hours at 4° C. The solubilized material is fractionated by gel filtration using Sepharose S-200 and the active peak pooled. The enzymatic activity is purified by affinity chromatography on DNA-cellulose equilibrated with 25 mM Triis pH 8.0 30 mM sodium chloride, 1 mM EDTA, 1 mM dithiothreitol, 0.3% Triton X-100, 3 mM sodium azide, washed extensively with the same buffer, and eluted with 1.0M sodium chloride in the same buffer. By SDS polyacrylamid-gel electrophoresis the enzyme is a doublet of 37/39 kDA.

EXAMPLE 2

*Mycoplasma hyopneumoniae* strain VPP-11, strain J, or P-57223 is grown in 1.0 liter of Friis medium to a density of approximately $10^9$ to $10^{10}$ color changing units per ml. The cells are removed by centrifugation and 231 grams solid ammonium sulphate is added to the supernatant on ice to achieve 40% saturation. The protein precipitate is harvested by centrifugation, resuspended in 17.5 mM potassium phosphate pH 7.0, 3 mM sodium azide and dialyzed extensively against the same buffer. The activity is further purified by ion-exchange chromatography on DEAE-cellulose where the active fraction does not bind. The enzymatic activity is purified by affinity chromatography on DNA-cellulose equilibrated with 25 mM Tris pH 8.0, 30 mM sodium chloride, 1 mM EDTA, 1 mM dithiothreitol, 0.3% Triton X-100, 3 mM sodium azide, washed extensively with the same buffer, and eluted with 1.0M sodium chloride in the same buffer. This is the DNA-cellulose fraction. By SDS polyacrylamide-gel electrophoresis the enzyme is a doublet of 37/39 kDa.

EXAMPLE 3

A 6 ml aliquot (total volume: 12 ml) of the DNA-cellulose fraction from Example 2 was combined with an equal volume of Freund's incomplete adjuvant through dropwise addition of the adjuvant while the resulting homogenate was constantly mixed by sonication.

Vaccinations

Miniature pigs are immunized sub-cutaneously in the hip with 2.0 ml aliquots of the vaccine plus adjuvant at the age of seven days, with a booster injection administered two weeks after the initial injection.

Challenge

Another group of pigs of the same age as the experimental animals were intratracheally innoculated with P-57223 *M. hyopneumaniae* at the age of three days and served as "seeder pigs" for the subsequent swine mycoplasmal pneumonia (MPS) challenge. Three weeks after the initial vaccination the experimental animals described above were commingled with the seeder pigs to initiate the transmission of *M. hyopneumoniae* by contact exposure. The animals remained together until necropsy, six weeks after the initiation of MPS challenge.

In the 6 non-vaccinates, there were two pigs with MPS lesions and four pigs with no lesions. In the 6 vaccinates, there were no pigs with MPS lesions and six pigs with no lesions.

EXAMPLE 4

Preparation of antibody

*M. hyopneumoniae* strain P-57223 was grown in 1 liter of Friis medium to a density of approximately $10^9$ to $10^{10}$ color changing units per ml. The cells were removed by centrifugation and solid ammonium sulphate was added to the growth culture supernatant to achieve 40% saturation at 0° C. The protein precipitate was harvested by centrifugation, resuspended in 17.5 mM potassium phospahte pH 7.0, 3 mM sodium azide and dialyzed extensively against the same buffer. The activity was further purified by ion-exchange chromatography on DEAE-cellulose and by affinity chromatography on DNA-cellulose as described previously.

Miniature pigs were immunized with 200 micrograms of DNA cellulose fraction in incomplete Freund's adjuvant. A booster injection was administered 2 weeks after the initial injection and the pigs were bled 2 weeks later. By Western blot analysis of total *M. hyopneumoniae* proteins, the antisera were shown to react at a 1:50 dilution with at least 6 proteins with apparent molecular weights betwen 26 and 97 kDa.

Such antisera may be employed in formulating a vaccine as hereinabove described.

Numerous modifications and variations of the present invention are possible in light of the above teachings and, therefore, within the scope of the appended claims, the invention may be practiced otherwise than as particularly described.

What is claimed is:

1. A method for protecting an animal against *M. hyopneumoniae*, comprising:
   administering to the animal at least one nuclease or fragment or derivative thereof which produces antibodies having paratopes which recognize extrinsic nuclease of *M. hyopneumoniae*, in an amount effective to protect said animal against *M. hyopneumoniae*.

2. The method of claim 1 wherein the nuclease is a DNase.

3. The method of claim 2 wherein the DNase is a DNA endonuclease.

4. The method of claim 1 wherein said animal is a swine.

5. The method of claim 1 wherein said administering is effected in a unit dosage form containing at least 5 micrograms of DNase, DNase fragment DNase derivative or mixture thereof.

6. A composition for protecting an animal against *M. hyopneumoniae*, comprising:
   a nuclease or fragment or derivative thereof which produces antibodies having paratopes which recognize an extrinsic nuclease of *M. hyopneumoniae*, and a carrier, said composition being essentially free of *M. hyopneumoniae* cells.

7. The composition of claim 6 wherein said nuclease or fragment or derivative thereof is present in an amount effective to provide protection against a disease caused by *M. hyopneumoniae*.

8. The composition of claim 6 wherein the nuclease is a DNase.

9. The composition of claim 8 wherein the DNase is a DNA endonuclease.

10. A method of protecting an animal against *M. hyopneumoniae*, comprising:
    administering to the animal a member selected from the group consisting of antibodies, antibody fragments, antibody derivatives, and mixtures thereof having paratopes which recognize extrinsic nuclease of *M. hyopneumoniae* in an amount effective to protect against *M. hyopneumoniae*.

11. The method of claim 10 wherein the nuclease is a DNase.

12. The method of claim 11 wherein the nuclease is a DNA endonuclease.

13. The method of claim 12 wherein said animal is a swine.

14. Extrinsic *M. hyopneumoniae* DNase having a molecular weight of from 35 Kda to 40 Kda, said DNase being essentially free of *M. hyopneumoniae* cells.

* * * * *